(12) United States Patent
Wong et al.

(10) Patent No.: US 8,809,587 B2
(45) Date of Patent: Aug. 19, 2014

(54) SYSTEMS AND METHODS FOR PRODUCING AROMATIC AMINES AND REMOVING PHENOL THEREFROM

(75) Inventors: Eric Wong, Houston, TX (US); Faisal Mohmand, Sugar Land, TX (US); Matthew R. Ulrich, Katy, TX (US)

(73) Assignee: Kellogg Brown & Root LLC, Houston, TX (US)

(*) Notice: Subject to any disclaimer, the term of this patent is extended or adjusted under 35 U.S.C. 154(b) by 129 days.

(21) Appl. No.: 13/178,595

(22) Filed: Jul. 8, 2011

(65) Prior Publication Data

US 2012/0172627 A1    Jul. 5, 2012

Related U.S. Application Data

(60) Provisional application No. 61/428,463, filed on Dec. 30, 2010.

(51) Int. Cl.
*C07C 209/00* (2006.01)
*C07C 209/84* (2006.01)
*C07C 209/36* (2006.01)

(52) U.S. Cl.
CPC ............. *C07C 209/36* (2013.01); *C07C 209/84* (2013.01)
USPC ........................................ 564/420

(58) Field of Classification Search
None
See application file for complete search history.

(56) References Cited

U.S. PATENT DOCUMENTS

| | | | |
|---|---|---|---|
| 2,292,879 A * | 8/1942 | Kise | 564/422 |
| 4,777,295 A | 10/1988 | Twigg | |
| 5,545,753 A | 8/1996 | Yasuhara et al. | |
| 7,049,471 B2 | 5/2006 | Renner et al. | |
| 7,692,042 B2 | 4/2010 | Dugal et al. | |
| 2005/0023212 A1 | 2/2005 | Inoue et al. | |
| 2006/0091014 A1 | 5/2006 | Inoue et al. | |
| 2007/0203364 A1 | 8/2007 | Dugal et al. | |
| 2007/0238901 A1 | 10/2007 | Dugal et al. | |
| 2009/0065347 A1 | 3/2009 | Sommer et al. | |
| 2010/0324336 A1 | 12/2010 | Sommer et al. | |

OTHER PUBLICATIONS

Carmona et al., Combined adsorption and ion exchange equilibrium of phenol on Amberlite IRA-420, Chemical Engineering Journal 117 (2006) 155-160, entire document.
Gross et al., Comparison of Different Atomic Charge Schemes for Predicting pKa Variations in Substituted Anilines and Phenois, International Journal of Quantum Chemistry, vol. 90, 445-458 (2002), entire document.
Acros Organics Material Study Data Sheet for Amberlite IRA-420, anion exchange resin MSDS# 71890, entrie document.

* cited by examiner

*Primary Examiner* — Clinton Brooks
(74) *Attorney, Agent, or Firm* — Gary M. Machetta

(57) ABSTRACT

Systems and methods for producing aromatic amines and removing phenol therefrom are provided. The method can include hydrogenating one or more aromatic nitro compounds to produce a reaction product comprising one or more aromatic amines, water, and phenol. The method can also include contacting the reaction product with one or more ion exchange materials to produce an aromatic amine product that contains less phenol than the reaction product. The one or more ion exchange materials can be solid, semi-solid, or a combination thereof.

16 Claims, 4 Drawing Sheets

SYSTEMS AND METHODS FOR PRODUCING AROMATIC AMINES AND REMOVING PHENOL THEREFROM

CROSS REFERENCE TO RELATED APPLICATION

This application claims the benefit of U.S. Provisional Patent Application having Ser. No. 61/428,463, filed on Dec. 30, 2010, which is incorporated by reference herein.

BACKGROUND

1. Field

Embodiments described herein generally relate to systems and methods for producing aromatic amines and removing phenol therefrom.

2. Description of the Related Art

Aromatic amines, including aniline, are precursors for the preparation of many industrial chemicals. The largest use of aniline is in the production of methylene diphenyl diisocyanate (MDI), which can be reacted with polyols to produce polyurethane. Aniline is typically produced by catalytically hydrogenating nitrobenzene under gas or liquid phase reaction conditions. In addition to aniline, several impurities are produced. These impurities need to be removed in order to produce an aniline product having acceptable purity.

Distillation is typically used to separate the impurities from crude aniline. Phenol, however, is a particularly difficult impurity to remove via distillation from the crude aniline because aniline and phenol have similar boiling points (184.1° C. and 181.7° C., respectively). As such, distillation towers capable of removing phenol from the crude aniline are complex and expensive to construct and operate. One method for separating phenol from crude aniline is to contact the crude aniline with an aqueous alkali metal hydroxide to convert the phenol to high boiling phenolates, which can then be separated via distillation. This approach, however, produces an aqueous phenolate-containing byproduct and/or residues that foul distillation reboilers. As such, a downstream system for purifying the aqueous phenol byproduct and/or frequent cleaning of the distillation reboilers is required.

There is a need, therefore, for improved systems and methods for producing aniline and removing phenol therefrom.

DETAILED DESCRIPTION

Figure 1:
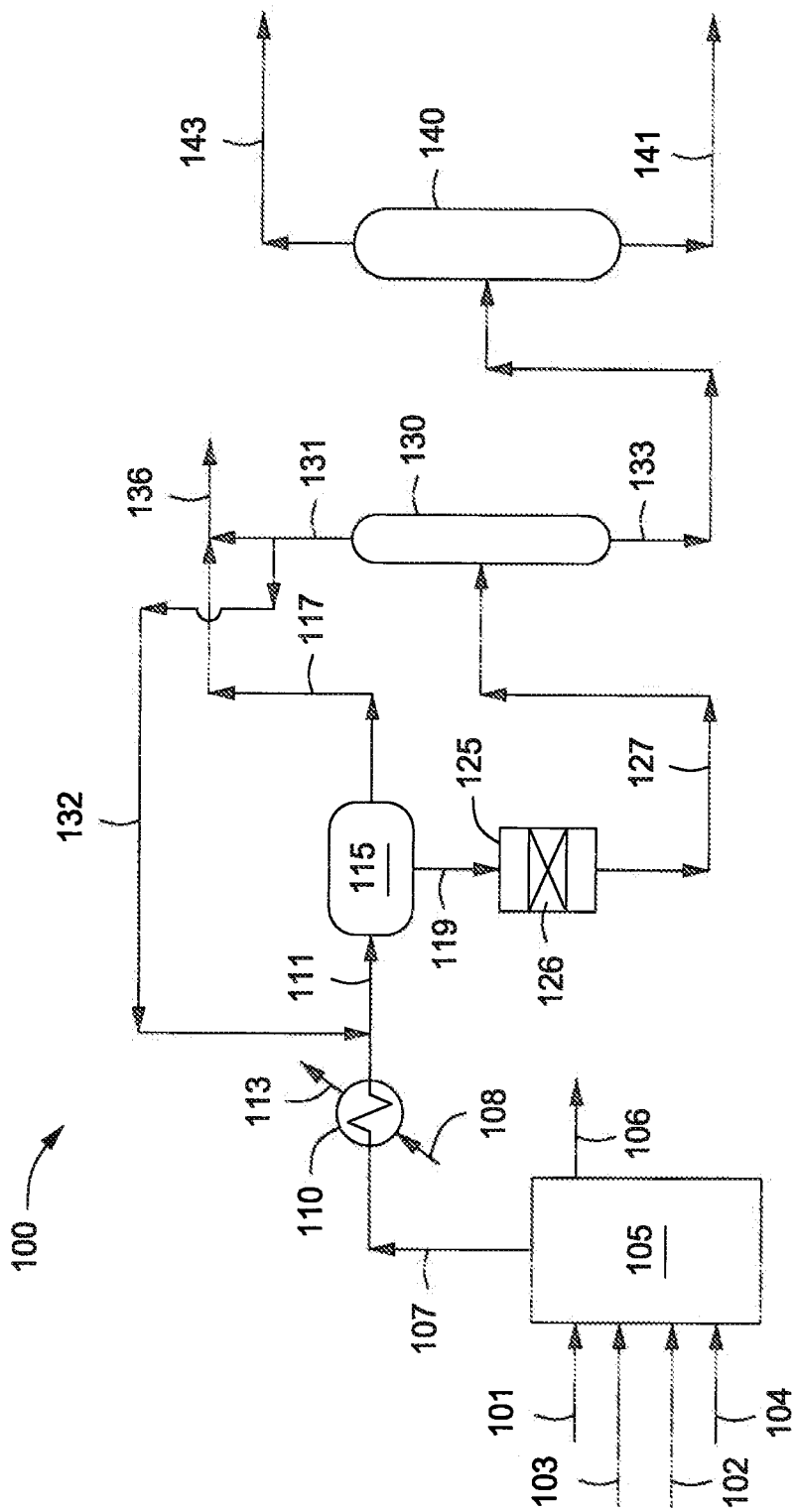
FIG. 1 depicts a schematic of an illustrative system for producing a crude aromatic amine and separating phenol therefrom, according to one or more embodiments described.

Systems and methods for producing aromatic amines and removing phenol therefrom are provided. The method can include hydrogenating one or more aromatic nitro compounds to produce a reaction product comprising one or more aromatic amines, water, and phenol. The method can also include contacting the reaction product with one or more ion exchange materials to produce an aromatic amine product that contains less phenol than the reaction product. The one or more ion exchange materials can be solid, semi-solid, or a combination thereof.

One or more aromatic nitro compounds can be hydrogenated to produce a raw aromatic amine product or "reaction product." The particular composition of the reaction product produced via hydrogenation can be at least partially based on the particular aromatic nitro compound or combination of aromatic nitro compounds that are hydrogenated. Illustrative aromatic nitro compounds can include, but are not limited to, nitrobenzene, nitrotoluene, dinitrotoluene (DNT), dinitrobenzene (DNB), or any combination thereof. As such, the raw aromatic amine product can include, but is not limited to, aniline, toluidine, toluenediamine (TDA), phenylenediamine, or any combination thereof.

The raw aromatic amine product or reaction product, before further purification or processing, can include a mixture of one or more aromatic amines and one or more impurities. Illustrative impurities can include, but are not limited to, water, phenol, nitrobenzene, benzene, nitrotoluene, dinitrotoluene (DNT), dinitrobenzene (DNB), polynitrobenzenes, methylcyclopentane, methylcyclohexane, mononitrotoluenes, nitroxylenes, cyclohexanone, cyclohexanol, cyclohexylamine, cyclohexanone, cyclohexylaniline, diphenylamines, phenylene diamines, cyclohexylidene aniline, toluidenes, xylidenes, toluene, or any combination thereof.

The hydrogenation or reduction of the aromatic nitro compound(s) can be carried out in a continuous, semi-continuous, and/or batch-wise manner. The hydrogenation of the aromatic amine(s) can be carried out under liquid phase conditions and/or gas phase conditions. The hydrogenation can be carried out at a temperature ranging from a low of about 30° C., about 50° C., or about 80° C. to a high of about 250° C., about 300° C., about 400° C., or about 500° C. The hydrogenation can be carried out at a pressure ranging from a low of about 101 kPa, about 150 kPa, or about 200 kPa to a high of about 1,000 kPa, about 2,000 kPa, about 3,500 kPa, or about 5,000 kPa. The reaction mixture of the aromatic nitro compound(s) can have a residence time during the hydrogenation ranging from about 1 minute to about three hours. The molar ratio of hydrogen to the aromatic nitro compounds can range from a low of about 3:1, about 3.2:1, or about 3.4:1 to a high of about 3.8:1, about 4:1, or about 4.2:1.

The hydrogenation of the aromatic nitro compound(s) can be carried out in the presence of one or more catalysts. Any suitable catalyst capable of promoting the hydrogenation of the aromatic nitro compound(s) can be used. Illustrative catalysts can include, but are not limited to, nickel, iron, chromium, platinum, copper, cobalt, palladium, rhodium, iridium, oxides thereof, hydroxides thereof, carbonates thereof, formates thereof, or any combination thereof. The catalyst(s) can be unsupported or supported. Illustrative support materials can include, but are not limited to, carbon, aluminum oxide, and the like. The concentration of catalyst on a support can range from a low of about 0.1 wt % to about 50 wt %, based on the weight of the support material. The support material can have a particle size ranging from about 0.01 μm to about 100 μm. The support material can have a surface area ranging from about 10 m² to about 1,000 m² per gram.

In addition to the one or more catalysts, the hydrogenation of the aromatic nitro compound(s) can be carried out in the presence of water and/or one or more aromatic amines. In one or more embodiments, the water and/or aromatic amines can provide at least some control over the temperature of the hydrogenation reaction and/or to can facilitate introduction of the catalyst. For example, the catalyst can be introduced with a carrier fluid, e.g., aniline and/or water, to a hydrogenation reactor or hydrogenation zone. Used, spent, and/or depleted catalyst can be recovered from the hydrogenation reactor or zone as a byproduct or waste product.

The aromatic nitro compound(s) and an aromatic amine/catalyst mixture can be introduced to the hydrogenation rector or zone at a weight ratio ranging from about 1:0.45 to about 1:0.6, about 1:0.5 to about 1:0.6, about 1:0.5 to about 1:0.55, or about 1:0.45 to about 1:0.55. The aromatic nitro compound(s) and the water can be introduced to the hydrogenation rector or zone at a weight ratio ranging from about 1:0.9 to about 1:1.25, about 1:1 to about 1:1.15, about 1:0.95 to about 1:1.1, or about 1:1 to about 1:1.1. The aromatic nitro compound(s) and hydrogen can be introduced to the hydrogenation rector or zone at a weight ratio ranging from about 30:1 to about 10:1, about 25:1 to about 10:1, about 20:1 to about 10:1, about 15:1 to about 10:1, or about 25:1 to about 12.5:1. The aromatic nitro compound(s) and an aromatic amine/catalyst mixture can be at a weight ratio ranging from about 1:0.5 to about 1:0.55, the aromatic nitro compound(s) and water can be at a weight ratio of about 1:1 to about 1:1.1, and the aromatic nitro compound(s) and hydrogen can be at a weight ratio of about 12.5:1 to about 25:1.

Illustrative processes for producing aromatic amines such as aniline are discussed and described in U.S. Pat. Nos. 7,049,471 and 7,692,042 and U.S. Patent Application Publication Nos.: 2007/0203364, 2007/0238901, and 2009/0065347.

In one or more embodiments, a suitable crude aromatic amine product or reaction product, e.g., aniline, can be produced by reacting one or more phenols with an amination agent. Illustrative phenols can include, but are not limited to, phenol, 2-methylphenol, 3-methylphenol, 4-methylphenol, o-, m- or p-isomers of ethylphenol and/or isopropylphenol, and alkyl phenols having at least one alkyl substituent, such as dimethylphenol, methylethylphenol, methylisopropylphenol, methylbutylpbenol, diethylphenol, ethylbutylphenol, diisopropylphenol, isopropylbutylphenol, dibutylphenol, or any combination thereof. Illustrative amination agents can include, but are not limited to, ammonia, ammonium carbonate, ammonium sulfate, ethylamine, n-propylamine, dimethylamine, diethylamine, diisopropylamine, methylethylamine, cyclohexylamine, aminopyridine, aniline, methylaniline, ethylaniline, n-propylaniline, isopropylaniline, dimethylaniline, diethylaniline, dipropylaniline, methylethylaniline, methylpropylaniline, or any combination thereof. An illustrative process for reacting one or more phenols with one or more amination agents is discussed and described in U.S. Pat. No. 5,545,753.

The reaction product can have a concentration of aromatic amine(s) ranging from about 15 wt % to about 80 wt %. For example, the amount of aromatic amine(s) in the reaction product can range from a low of about 20 wt %, about 25 wt %, about 35 wt %, or about 45 wt % to a high of about 60 wt %, about 65 wt %, about 70 wt %, or about 75 wt %. The reaction product can have a concentration of water ranging from about 25 wt % to about 85 wt %. For example, the amount of water in the reaction product can range from a low of about 25 wt %, about 40 wt %, about 45 wt %, or about 50 wt % to a high of about 60 wt %, about 65 wt %, about 70 wt %, or about 75 wt %. The reaction product can have a phenol concentration ranging from about 1 part per million by weight (ppmwt) to about 1,500 ppmwt. For example, the amount of phenol in the reaction product can range from a low of about 1 ppmwt, about 50 ppmwt, or about 100 ppmwt to a high of about 800 ppmwt, about 1,000 ppmwt, or about 1,200 ppmwt. The reaction product can have a combined impurity concentration (excluding phenol and water) ranging from about 1 ppmwt to about 8,000 ppmwt. For example, the amount of impurities other than phenol and water in the reaction product can range from a low of about 1 ppmwt, about 100 ppmwt, or about 250 ppmwt to a high of about 1,000 ppmwt, about 5,000 ppmwt, or about 8,000 ppmwt. In one or more embodiments, the reaction product can include about 35 wt % to about 45 wt % aromatic amines and about 55 wt % to about 65 wt % water, and less than about 5 wt % other components.

In one or more embodiments, the reaction product as produced, after cooling, and/or after any one or more other subsequent purification processes, can be contacted with one or more ion exchange materials to produce a phenol-lean product. In other words, the reaction product or a cooled and/or purified reaction product can be contacted with the one or more ion exchange materials to produce a phenol-lean product that contains less phenol than the reaction product. For example, some or most of the water, e.g., from about 1% to about 99.999%, contained in the reaction product can be removed and then the reaction product containing less water can be contacted with the one or more ion exchange materials to produce the phenol-lean product.

The ion exchange material can be or include any material or combination(s) of materials containing one or more charged groups or ions that can be exchanged for the negatively charged OH group of the phenol molecules contained in the crude product. Upon contact with the crude product, the ion exchange material(s) can bind with the phenol molecules contained in the crude product. For example, the ion exchange material can convert the phenol molecule to a phenate molecule and in the process bind the phenate molecule thereto, thereby removing the phenol molecule from the crude product. Illustrative functional groups the ion exchange materials can include or have, can be, but are not limited to, $OH^-$, $F^-$, $HCO_3^-$, $Cl^-$, $Br^-$, $NO_3^-$, $HSO_4^-$, $PO_4^{3-}$, $CrO_4^{2-}$, $CO_3^-$, and $SO_4^{2-}$. In at least one specific embodiment, the ion exchange material preferably includes one or more $OH^-$ functional groups.

Illustrative ion exchange materials can include, but are not limited to, polymers or resins, bases or alkaline compounds, zeolites impregnated and/or coated with one or more inorganic ions, or any combination thereof. Suitable zeolites can be impregnated and/or coated with one or more inorganic ions, e.g., zeolites containing sodium hydroxide. Suitable bases can include, but are not limited to, hydroxides, carbonates, amines, or any combination thereof. Illustrative hydroxides can include, but are not limited to, sodium hydroxide, potassium hydroxide, ammonium hydroxide (e.g., aqueous ammonia), lithium hydroxide, and cesium hydroxide. Illustrative carbonates can include, but are not limited to, sodium carbonate, potassium carbonate, and ammonium carbonate.

Other suitable amines can include, but are not limited to, primary amines ($NH_2R_1$), secondary amines ($NHR_1R_2$), and tertiary amines ($NR_1R_2R_3$), where each $R_1$, $R_2$, and $R_3$ can be independently selected from alkyls, cycloalkyls, heterocloalkyls, aryls, heteroaryls, and substituted aryls. The alkyl can include branched or unbranched alkyls having from 1 to 15 carbon atoms or more preferably from 1 to 8 carbon atoms. Illustrative alkyls can include, but are not limited to, methyl, ethyl, n-propyl, isopropyl, n-butyl, sec butyl, t-butyl, n-pentyl, n-hexyl, and ethylhexyl. The cycloalkyls can include from 3 to 7 carbon atoms. Illustrative cycloalkyls can include, but are not limited to, cyclopentyl, substituted cyclopentyl, cyclohexyl, and substituted cyclohexyl. The term "aryl" refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. In one or more embodiments, aryl substituents can have from 1 to about 20 carbon atoms. The term "heteroatom-containing," as in a "heteroatom-containing cycloalkyl group," refers to a molecule or molecular fragment in which one or more carbon atoms is replaced with an atom other than carbon, e.g., nitrogen, oxygen, sulfur, phosphorus, boron, or silicon. Similarly, the term "heteroaryl" refers to an aryl substituent that is heteroatom-containing. The term "substituted," as in "substituted aryls," refers to a molecule or molecular fragment in which at least one hydrogen atom bound to a carbon atom is replaced with one or more substituents that are functional groups such as hydroxyl, alkoxy, alkylthio, phosphino, amino, halo, silyl, and the like. Illustrative primary amines can include, but are not limited to, methylamine and ethylamine. Illustrative secondary amines can include, but are not limited to, dimethylamine and diethylamine. Illustrative tertiary amines can include, but are not limited to, trimethylamine and triethylamine.

A suitable ion exchange material can be or include cross-linked polystyrene that has been aminated to form a weakly basic or more preferably a strongly basic anion exchange resin. For example, the ion exchange material can be or include a polymer based on a cross-linked styrene divinylbenzene copolymer containing tertiary or quaternary ammonium groups. The ion exchange resins can be converted into cross-linked resins with conventional free radical addition catalysts such as peroxides. The chloro groups of the copolymer can be replaced by a condensation reaction with a secondary or tertiary alkylamine, arylamine, or alkyarylamine, where each alkyl includes 1 to 20 carbon atoms and each aryl includes 6 to 12 carbon atoms. Suitable tertiary ammonium groups can be produced by reacting the chloro groups of the copolymer with a secondary amine. Suitable quaternary amino ion exchange resins can be formed by reacting the chlor groups of the copolymer with a tertiary amine. Quaternization of the tertiary amine containing resin can be carried out by, e.g., reaction with a hydrocarbon halide such as an alkyl halide or an aryl halide to form the corresponding quaternary amine halide. The polymer based on a cross-linked styrene divinylbenzene copolymer containing tertiary or quaternary ammonium groups can contain $OH^-$ functional groups. The ion exchange material that includes a polymer based on a cross-linked styrene divinylbenzene copolymer containing quaternary ammonium groups can also include water, e.g., water ranging in an amount of about 35 wt % to about 75 wt %, about 40 wt % to about 70 wt %, or about 45 wt % to about 65 wt % based on the total weight of the polymer and the water. Polymers based on a cross-linked styrene divinylbenzene copolymer containing tertiary or quaternary ammonium groups can be of the macroreticular type as described in, for example, Kirk-Othmer, Encyclopedia of Chemical Technology, Vol. 13, p. 689, 1981, John Wiley and Sons, Inc. In another example, the ion exchange material can be or include one or more tertiary amine resins. Suitable, commercially available ion exchange resins can include, but are not limited to, AMBERLYST® A26OH, available from the Rohm and Haas Company, and PUROLITE® A500, available from the Purolite Company.

In one or more embodiments, the ion exchange material can be solid, semi-solid, or a combination of solid and semi-solid structures. For example, the ion exchange material can be in the form of solid particles, semi-solid particles, e.g., a gelled particle, macroporous particles, microporous particles, or any combination thereof. The solid ion exchange material can be in the form of pellets, beads, granules, flakes, spheres, cubes, blocks, fibers, filaments, threads, or any combination thereof. In another example, ion exchange material including one or more bases, e.g., sodium hydroxide and/or potassium hydroxide, can be in the form of pellets or granules. As used herein, the terms "semi-solid" and "semi-solid particle" refer to a three-dimensional structure that itself is insoluble in a particular liquid. The three-dimensional structure can be capable of absorbing and retaining a quantity of the liquid to form a stable, often soft and pliable structure. The ion exchange material can be solid and/or semi-solid structures disposed within a fixed bed, a fluid or moving bed, or a combination thereof. In another example, the solid and/or semi-solid structures can be supported on one or more support members such as a rigid support member, between two or more support members such as screens, plates, and the like, or any combination thereof.

The ion exchange material disposed within a fixed bed can have a bed depth ranging from a low of about 5 cm, about 10 cm, about 20 cm, about 30 cm, or about 40 cm to a high of about 70 cm, about 85 cm, about 100 cm, about 150 cm, about 200 cm, or about 300 cm. For example, the ion exchange material can be disposed within a fixed bed having a bed depth of about 40 cm to about 80 cm, about 50 cm to about 70 cm, about 60 cm to about 120 cm, about 60 cm to about 200 cm, or about 90 cm to about 250 cm. The fixed bed containing the ion exchange material can be disposed within a contact vessel or "phenol extraction unit." The phenol extraction unit can contain or otherwise include one, two, four, six, eight, ten, twelve, fifteen, twenty, or more discrete or separate fixed beds. Any number of phenol extraction units each having any number of fixed beds disposed therein can be arranged in series, parallel, or both with respect to one another. The number of fixed beds, the size of the fixed beds, and the particular ion exchange material disposed within each fixed bed can be the same or different between any two phenol extraction units.

The average cross-sectional size or length of the ion exchange material, e.g., ion exchange resins, can range from a low of about 0.01 mm, about 0.05 mm, about 0.1 mm, about 0.3 mm, or about 0.5 mm to a high of about 1 mm, about 2 mm, about 3 mm, about 5 mm, about 7 mm, about 9 mm, about 11 mm, about 13 mm, about 15 mm, or about 20 mm. In one or more embodiments, the ion exchange material, e.g., ion exchange resins, can have an average pore diameter ranging from a low of about 20 angstroms (Å), about 50 Å, or about 100 Å to a high of about 200 Å, about 300 Å, about 400 Å, or about 500 Å. For example, the ion exchange material can have an average pore diameter of about 200 Å to about 400 Å, or about 150 Å to about 300 Å, or about 225 Å to about 450 Å. In one or more embodiments, the ion exchange material, e.g., ion exchange resins, can have a pore volume ranging from a low of about 0.05 ml/g, about 0.1 ml/g, or about 0.15 ml/g to a high of about 0.3 ml/g, about 0.5 ml/g, or about 1 ml/g. For example, the ion exchange material can have a pore volume about 0.15 ml/g to about 0.25 ml/g, about 0.2 ml/g to about 0.4 ml/g, or about 0.2 ml/g to about 1 ml/g. In one or more embodiments, the ion exchange material, e.g., ion exchange resins, can have a surface area ranging from a low of about 10 $m^2/g$, about 15 $m^2/g$, or about 20 $m^2/g$ to a high of about 30 $m^2/g$, about 40 $m^2/g$, or about 50 $m^2/g$.

Depending, at least in part, on the particular ion exchange material and/or the amount of phenol contained in the crude product, the crude product can be contacted with the ion exchange material at a rate of about 0.1 $m^3$ crude product per 1 $m^3$ ion exchange material per hour to about 35 $m^3$ crude product per 1 $m^3$ ion exchange material per hour. For example, the crude product can be contacted with the ion exchange material at a rate ranging from a low of about 1 m³, about 3 m³, about 5 m³, or about 10 m³ to a high of about 15 m³, about 20 m³, about 25 m³, or about 30 m³ crude product per 1 m³ ion exchange material per hour. In another example, the crude product can be contacted with the ion exchange material at a rate ranging from about 1 m³ to about 8 m³ crude product per 1 m³ ion exchange material per hour, from about 2 m³ to about 4 m³ crude product per 1 m³ ion exchange material per hour, from about 3 m³ to about 5 m³ crude product per 1 m³ ion exchange material per hour, about 4 m³ to about 6 m³ crude product per 1 m³ ion exchange material per hour, about 10 m³ to about 27 m³ crude product per 1 m³ ion exchange material per hour. In one or more embodiments, the ion exchange material can remain in the solid or semi-solid form upon and after contact with the crude product or the crude produce after refining, purifying, or otherwise processing the crude product, e.g., separating water from the crude product to produce a dehydrated product.

Depending, at least in part, on the particular ion exchange material, the crude product can be contacted therewith at a temperature ranging from a low of about 20° C., about 30° C., or about 40° C. to a high of about 60° C., about 80° C., or about 100° C. In another example, the crude product can be contacted with the ion exchange material(s) at a temperature ranging from a low of about −5° C., about 0° C., or about 5° C., to a high of about 10° C., about 20° C., about 50° C., about 75° C., or about 90° C. Depending, at least in part, on the particular ion exchange material, the crude product can be at a pressure ranging from a low of about 101 kPa, about 200 kPa, or about 500 kPa to a high of about 1,000 kPa, about 1,200 kPa, or about 2,000 kPa when contacted therewith.

In one or more embodiments, when the capacity of the ion exchange material nears exhaustion, i.e., the ion exchange material no longer removes a sufficient amount of phenol from the crude product, the ion exchange material can be replaced with a new ion exchange material. In one or more embodiments, when the capacity of the ion exchange material nears exhaustion, the ion exchange material can be regenerated. For example, contacting the crude aniline with the ion exchange material can be stopped or diverted elsewhere, e.g., another location containing another ion exchange material and one or more regenerate materials can be contacted with the exhausted ion exchange material. Illustrative regenerate materials can include one or more hydroxide solutions. Hydroxide solutions suitable for regenerating the ion exchange material can include, but are not limited to, sodium hydroxide, potassium hydroxide, ammonium hydroxide (e.g., aqueous ammonia), lithium hydroxide, cesium hydroxide, or any combination thereof. The regenerate material(s) can remove and replace the phenate molecules bound to the ion exchange material with the desired functional group, thereby regenerating the ion exchange material. The regenerate material(s) can be liquid or gaseous fluids. For example, the regenerate material(s) can include aqueous hydroxide solutions, e.g., aqueous sodium hydroxide and/or aqueous potassium hydroxide.

In one or more embodiments, the reaction product can be cooled to produce a cooled reaction product. For example, heat from the reaction product can be indirectly transferred to a heat transfer medium to produce the cooled reaction product and a heated heat transfer medium. Illustrative heat transfer mediums can include, but are not limited to, cooling water, boiler feed water, low pressure steam, medium pressure steam, glycols, air and/or other gaseous fluids, or any combination thereof. In another example, the reaction product can be cooled by direct contact or mixing with a cooling fluid such as water to produce the cooled reaction product. In one or more embodiments, the reaction product can be cooled by a combination of indirect heat exchange and direct contact cooling.

The cooled reaction product can be at a temperature ranging from a low of about 0° C., about 25° C., about 50° C., or about 75° C. to a high of about 150° C., about 175° C., or about 200° C. The cooled reaction product can be at a pressure ranging from a low of about 101 kPa, about 300 kPa, or about 500 kPa to a high of about 1,000 kPa, about 1,500 kPa, or about 2,000 kPa.

In one or more embodiments, a first portion of the water in the cooled reaction product can be separated therefrom to produce a crude product. The crude product can have a concentration of aromatic amine(s) ranging from about 85 wt % to about 99 wt %. For example, the amount of aromatic amine(s) in the crude product can range from a low of about 85 wt %, about 90 wt %, about 92 wt %, or about 93 wt % to a high of about 96 wt %, about 97 wt %, about 98 wt %, or about 99 wt %. The crude product can have a concentration of water ranging from about 0.1 wt % to about 15 wt %. For example, the amount of water in the crude product can range from a low of about 0.1 wt %, about 1 wt %, or about 2 wt % to a high of about 5 wt %, about 8 wt %, about 10 wt %, or about 12 wt %. The crude product can have a phenol concentration ranging from about 1 ppmwt to about 2,000 ppmwt. For example, the amount of phenol in the crude product can range from a low of about 1 ppmwt, about 50 ppmwt, or about 100 ppmwt to a high of about 800 ppmwt, about 1,000 ppmwt, about 1,200 ppmwt, or about 1,600 ppmwt. The crude product can have a combined impurity concentration (excluding phenol and water) ranging from about 1 ppmwt to about 10,000 ppmwt. For example, the amount of impurities other than phenol and water in the crude product can range from a low of about 1 ppmwt, about 100 ppmwt, or about 250 ppmwt to a high of about 1,000 ppmwt, about 5,000 ppmwt, or about 8,000 ppmwt.

In one or more embodiments, at least a portion of the phenol can be separated from the crude product to produce a phenol-lean crude product. For example, at least a portion of the crude product can be contacted with one or more ion exchange materials. Contacting the crude product with the ion exchange material(s) can remove about 80% or more, about 85% or more, about 90% or more, about 95% or more, or about 99.9% or more of the phenol contained in the crude product. For example, the amount of the phenol contained in the crude product removed by contacting the crude product with the ion exchange material(s) can range from a low of about 90%, about 93%, about 94%, or about 96% to a high of about 97%, about 98%, about 99%, about 99.9%, or about 99.99%. As such, the phenol-lean crude product can have a phenol concentration of less than about 200 ppmwt, less than about 100 ppmwt, less than about 50 ppmwt, less than about 30 ppmwt, less than about 20 ppmwt, less than about 10 ppmwt, less than about 5 ppmwt, less than about 3 ppmwt, less than about 2 ppmwt, or less than about 1 ppmwt.

The phenol-lean crude product can be dehydrated to separate at least a portion of any remaining water contained in the phenol-lean crude product to produce a dehydrated crude product. For example, the phenol-lean crude product can be distilled, fractionated, stripped, or otherwise separated to produce the dehydrated crude product. The dehydrated crude product can have an aromatic amine(s) concentration ranging from a low of about 96 wt %, about 97 wt %, or about 98 wt % to a high of about 99 wt %, about 99.9 wt %, about 99.99 wt %, or about 99.999 wt %. The dehydrated crude product can have a water concentration ranging from a low of about 1 ppmwt, about 100 ppmwt, or about 200 ppmwt to a high of about 1,000 ppmwt, about 1,500 ppmwt, or about 2,000 ppmwt. The dehydrated crude product can have a combined impurity concentration (excluding phenol and water) ranging from a low of about 1 ppmwt, about 100 ppmwt, or about 250 ppmwt to a high of about 1,000 ppmwt, about 5,000 ppmwt, or about 15,000 ppmwt.

In the context of an aromatic amine product that contains aniline or contains aniline as a majority component, the dehydration of the phenol-lean crude product can be carried out at a temperature of at least about 100° C. and up to about 180° C. Heating the phenol-lean crude product can vaporize the water and any other impurities such as toluene, cyclohexanol, methylcyclopentane, methylcyclohexane, and/or cyclohexylamine having a boiling point less than the temperature used for the dehydration. As such, impurities in addition to the separated water can be at least partially separated from the phenol-lean crude product. In this example, the aniline can remain a liquid or at least a majority of the aniline can remain in the liquid phase, thereby separating the lighter components such as water therefrom.

The dehydrated crude product can be further purified to produce a final or purified aromatic amine(s) product and a waste or heavies byproduct. For example, at least a portion of any remaining impurities can be separated from the dehydrated crude product. The remaining impurities can include those impurities having a boiling point greater than the aromatic amine(s). In the context of an aromatic amine product that contains aniline or contains aniline as a majority component, the further purification of the dehydrated crude product can be carried out at a temperature ranging from about 140° C. to about 215° C. and a pressure ranging from about 5 kPa to about 150 kPa. For example, the dehydrated crude product can be heated to a temperature of about 145° C. to about 190° C., about 155° C. to about 210° C., or about 150° C. to about 195° C. while under a vacuum. As such, the aniline can be vaporized and the impurities or at least a majority of the impurities having a boiling point greater than aniline can remain condensed or in the liquid phase, thereby separating the higher boiling components or impurities from the aniline. The impurities can include, for example, nitrobenzene, polynitrobenzenes, mononitrotoluenes, diphenylamines, phenylene diamines, and the like.

The aromatic amine(s) product can have an aromatic amine(s) concentration of about 99 wt % or more, about 99.5 wt % or more, about 99.8 wt % or more, about 99.9 wt % or more, about 99.95 wt % or more, about 99.99 wt % or more, about 99.995 wt % or more, or about 99.999 wt % or more. The aromatic amine(s) product can have a water concentration of less than about 2,000 ppmwt, less than about 1,500 ppmwt, less than about 1,000 ppmwt, less than about 500 ppmwt, less than about 200 ppmwt, less than about 100 ppmwt, less than about 50 ppmwt, less than about 25 ppmwt, or less than about 10 pprnwt. For example, the aromatic amine(s) product can have a concentration of water ranging from about 1 ppmwt to about 500 ppmwt, about 1 ppmwt to about 50 ppmwt, about 10 ppmwt to about 100 ppmwt, or about 20 ppmwt to about 200 ppmwt. The aromatic amine(s) product can have a phenol concentration of less than about 200 ppmwt, less than about 100 ppmwt, less than about 50 ppmwt, less than about 30 ppmwt, less than about 20 ppmwt, less than about 10 ppmwt, less than about 5 ppmwt, less than about 3 ppmwt, less than about 2 ppmwt, or less than about 1 ppmwt. The aromatic amine(s) product can have a concentration of impurities (excluding water and phenol) of less than about 1,000 ppmwt, less than about 500 ppmwt, less than about 250 ppmwt, less than about 100 ppmwt, less than about 50 ppmwt, less than about 25 ppmwt, less than about 15 ppmwt, less than about 10 ppmwt, less than about 5 ppmwt, or less than about 1 ppmwt.

FIG. 1 depicts a schematic of an illustrative system 100 for producing a crude aromatic amine and separating phenol therefrom, according to one or more embodiments. One or more aromatic nitro compounds via line 101 and hydrogen via line 103 can be introduced to one or more hydrogenation reactor systems (one is shown 105) to produce a raw aromatic amine product or "reaction product" via line 107. The reaction product via line 107 can be a gas, liquid, or a combination thereof. In one or more embodiments, water via line 102 and/or one or more aromatic amines, e.g., aniline, via line 104 can also be introduced to the hydrogenation reactor system 105. The water via line 102 can act as a quench fluid or medium that can be used to regulate or otherwise adjust a temperature within the hydrogenation reactor system 105. The aniline via line 104 can be used as a carrier fluid for one or more catalysts. As such, the aniline via line 104 can also include one or more catalysts therein. In another example, the one or more catalysts can be introduced with the water via line 102 and aniline or any other aromatic amine(s) can be introduced via line 104. A byproduct or waste product via line 106 can also be recovered from the hydrogenation reactor system 105. The byproduct or waste product via line 106 can be a gas, liquid, or a combination thereof. The byproduct can include water, used, spent, or depleted catalyst, unreacted aromatic nitro compound(s), phenol, impurities, aromatic amines, or any combination thereof.

The amount of the one or more aromatic nitro compounds via line 101, hydrogen via line 103, water via line 102, and/or the aromatic amine/catalyst via line 104 introduced to the hydrogenation reactor system 105 can be constant or can vary. The particular aromatic nitro compounds in line 101 can influence the particular ratio of any two or more of the components introduced to the hydrogenation reactor system 105, e.g., the amount of the one or more aromatic nitro compounds via line 101, hydrogen via line 103, water via line 102, and/or aromatic amine/catalyst via line 104. In one or more embodiments, the ratios of the one or more aromatic nitro compounds via line 101, hydrogen via line 103, water via line 102, and/or the aromatic amine/catalyst via line 104 can be adjusted or otherwise controlled to produce a desired reaction product via line 107. In one or more embodiments, the aromatic nitro compound(s) via line 101 and the aromatic amine/catalyst via line 104 can be introduced to the hydrogenation reactor system 105 at a weight ratio ranging from about 1:0.45 to about 1:0.6, about 1:0.5 to about 1:0.6, about 1:0.5 to about 1:0.55, or about 1:0.45 to about 1:0.55. In one or more embodiments, the aromatic nitro compound(s) via line 101 and the water via line 102 can be introduced at a weight ratio ranging from about 1:0.9 to about 1:1.25, about 1:1 to about 1:1.15, about 1:0.95 to about 1:1.1, or about 1:1 to about 1:1.1. In one or more embodiments, the aromatic nitro compound(s) via line 101 and the hydrogen via line 103 can be introduced to the hydrogenation reactor system 105 at a weight ratio ranging from about 30:1 to about 10:1, about 25:1 to about 10:1, about 20:1 to about 0:1, about 15:1 to about 10:1, or about 25:1 to about 12.5:1.

As discussed above, the particular composition of the raw aromatic product via line 107 can be based on the particular aromatic nitro compound(s) introduced via line 101 to the hydrogenation reactor system 105. The reaction product via line 107 can include a mixture of one or more aromatic amines and one or more impurities. The impurities can include those discussed and described above, such as water, phenol, nitrobenzene, nitrotoluene, dinitrotoluene (DNT), dinitrobenzene (DNB), polynitrobenzenes, methylcyclopentane, methylcyclohexane, mononitrotoluenes, nitroxylenes, cyclohexanone, cyclohexanol, cyclohexylamine, cyclohexylaniline, diphenylamines, phenylene diamines, cyclohexylidene aniline, toluidenes, xylidenes, toluene, or any combination thereof.

In one or more embodiments, the reaction product via line 107 can be introduced to one or more heat exchangers (one is shown 110) to produce a cooled reaction product via line 111. For example, the reaction product via line 107 and a heat transfer medium via line 109 can be introduced to the heat exchanger 110 where heat can be indirectly transferred from the reaction product to the heat transfer medium to produce the cooled reaction product via line 111 and a heated heat transfer medium via line 113. Illustrative heat transfer mediums can include, but are not limited to, cooling water, boiler feed water, low pressure steam, medium pressure steam, glycols, air and/or other gaseous fluids, or any combination thereof. If boiler feed water is used as the heat transfer medium via line 108, steam can be recovered via line 113. For example, boiler feed water via line 108 can be heated within the heat exchanger 110 to produce low pressure steam, medium pressure steam, and/or high pressure steam via line 113. The one or more heat exchangers 110 can be or include one or more shell-and-tube, plate and frame, spiral wound, U-tube, bayonet style heat exchangers, or any combination thereof. In one or more embodiments, the reaction product via line 107 can be cooled by direct contact or mixing (not shown) with a cooling fluid such as water to produce the cooled reaction product via line 111. In one or more embodiments, the reaction product via line 107 can be cooled by a combination of indirect heat exchange and direct contact cooling.

The cooled reaction product via line 111 can be introduced to one or more phase separators (one is shown 115) where at least a portion of any water present in the reaction product can be separated therefrom. Separated water via line 117 and a crude product via line 119 can be recovered from the phase separator 115. Any type of separator capable of separating water from the crude product can be used. For example, the phase separator 115 can be an empty vessel and a sufficient residence time of the cooled reaction product within the phase separator 115 can produce the separated water via line 117 and the crude product via line 119. In another example, the phase separator 115 can include one or more walls, for example a plurality of horizontally or inclined spaced walls or plates disposed therein, which can increase the rate at which the water separates from the crude product. In still another example, the phase separator 115 can be or include one or more fractionation columns, distillation columns, or the like, or any combination thereof. In yet another example, the phase separator 115 can include one or more wire mesh coalescers.

The crude product via line 119 can be introduced to one or more phenol extraction units (one is shown 125) to produce a phenol-lean crude product via line 127. The phenol extraction unit 125 can include one or more ion exchange materials 126. The one or more ion exchange materials 126 can be as discussed and described above or elsewhere herein. For example, the one or more ion exchange materials can include one or more ion exchange resins. The one or more ion exchange materials can be in the form of solid particles, semi-solid particles, e.g., a gelled particle, macroporous particles, microporous particles, or any combination thereof. For example, the ion exchange material can be in the form of pellets, beads, granules, flakes, spheres, cubes, blocks, fibers, filaments, threads, or any combination thereof. The particles can be disposed within a fixed bed, a fluid or moving bed, or a combination thereof. In another example, the particles can be supported on a rigid support, between support structures such as screens, and the like.

The phenol-lean crude product via line 119 can be introduced to one or more dehydration columns (one is shown 130), which can separate at least a portion of any remaining water and/or other impurities contained in the phenol-lean crude product. The separated water via line 131 and a dehydrated crude product via line 133 can be recovered from the dehydration column 130. The separated water via line 131 can be mixed or otherwise combined with the water recovered from the phase separator 110 via line 117 to provide a recovered water byproduct via line 136. In another example, the separated water in line 131 can include some free aniline, as such, all or a portion of the separated water in line 131 can be recycled via line 132 to the cooled reaction product in line 111. The recovered water byproduct via line 136 can be recycled to one or more locations within the hydrogenation reactor 105, the phase separator 115, treated for disposal, or any combination thereof.

The dehydration column 130 can include any system, device, or combination of systems and/or devices capable of separating at least a portion of any water contained in the phenol-lean crude product introduced thereto via line 127. For example, the dehydration column 130 can be or include one or more distillation columns or fractionation columns. The dehydration column 130 can be operated at a temperature of at least about 100° C. up to about 215° C., which can vaporize at least a portion of the water and any other impurities such as toluene, benzene, cyclohexanol, methylcyclopentane, methylcyclohexane, cyclohexanone, and/or cyclohexylamine having a boiling point less than the temperature within the dehydration column 130. As such, impurities in addition to the separated water can be recovered via line 136.

The dehydration column 130 can be empty, partially filled, or completely filled with one or more materials to improve mass transfer and/or separation of the water from the phenol-lean crude product. For example, the fill material can include, but is not limited to, structured materials, random packed materials, trays, or any combination thereof. Two or more types of fill material can be disposed within the dehydration column 130. For example, the dehydration column 130 can contain random dumped packing and one or more trays.

As used herein, the term "trays" can include, but is not limited to, one or more types of trays that can improve the contact between gas and/or liquid phases within the dehydration column 130. Illustrative trays can include, but are not limited to perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof. As used herein, the term "packing material" can include, but is not limited one or more types of structured and/or random shaped material disposed within the dehydration column 130. The packing material can increase the effective surface area within the dehydration column 130, which can improve the mass transfer between liquid and/or gas phases within the dehydration column 130. The packing material can be made of any suitable material, for example metals, non-metals, polymers, ceramics, glasses, or any combination thereof. Illustrative examples of random packing material can include, but are not limited to, Raschig rings, Lessing rings, I-rings, saddle rings, Intalox saddles, Tellerettes, Pall rings, U-rings, or any combination thereof. Illustrative examples of commercially available structured packing can include, but are not limited to, structured packing, corrugated sheets, crimped sheets, gauzes, grids, wire mesh, monolith honeycomb structures, or any combination thereof.

The dehydrated crude product via line 133 can be introduced to one or more product columns (one is shown 140) to produce a final or purified aromatic amine product via line 143 and a waste or heavies byproduct via line 141. The product column 140 can be similar to the dehydration column 130. For example, the product column 140 can include any system, device, or combination of systems and/or devices capable of separating at least a portion of the impurities from the aromatic amine(s) in the dehydrated product introduced thereto via line 133. For example, the product column 140 can be or include one or more distillation columns or fractionation columns. The product column 140 can be empty, partially filled, or completely filled with one or more trays and/or packing material to improve mass transfer and/or separation of the aniline from the dehydrated product.

Figure 2:
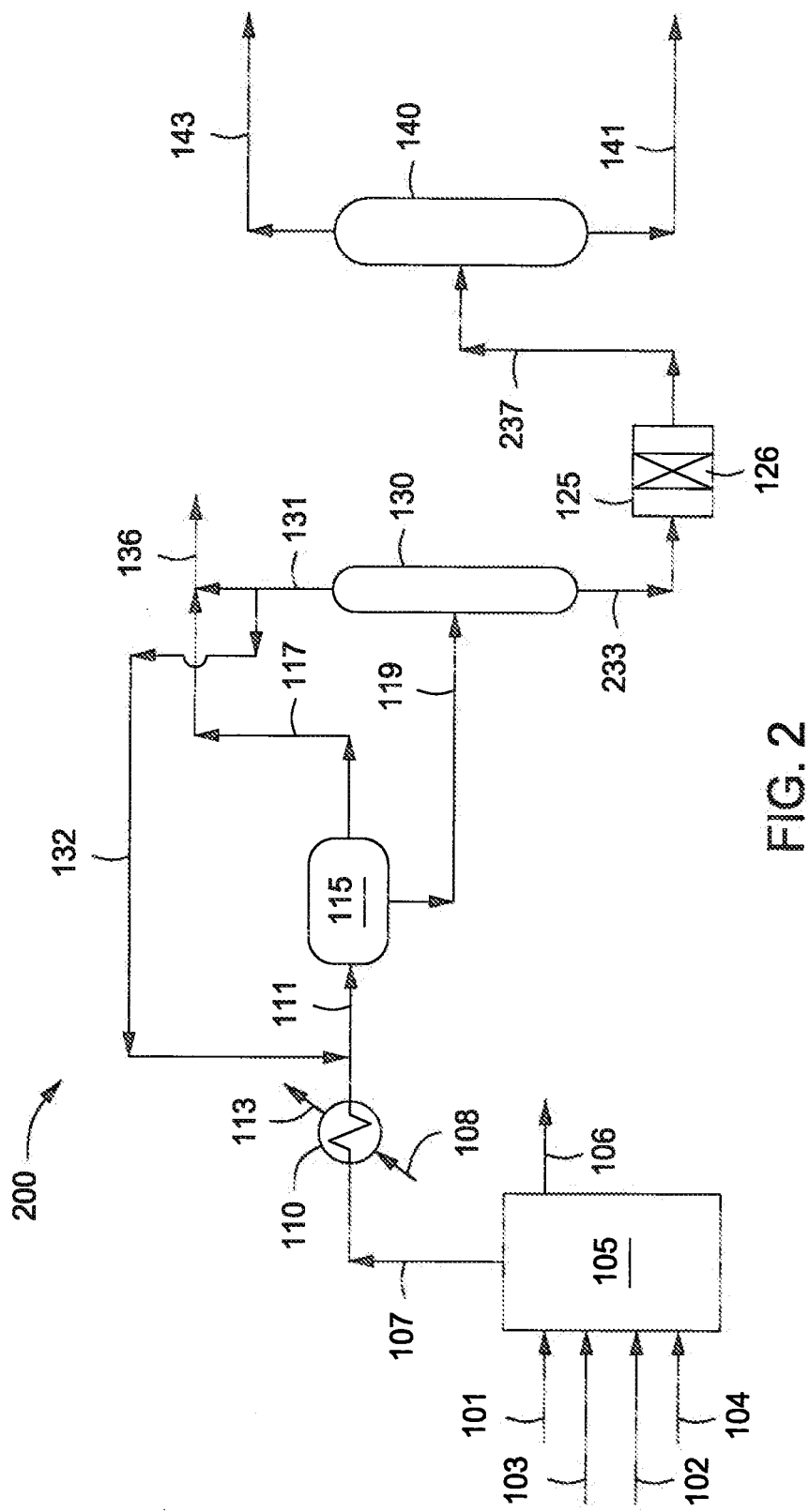
FIG. 2 depicts a schematic of another illustrative system for producing a crude aromatic amine and separating phenol therefrom, according to one or more embodiments described.

FIG. 2 depicts a schematic of another illustrative system 200 for producing a crude aromatic amine and separating phenol therefrom, according to one or more embodiments. The system 200 can include the one or more hydrogenation reactors 105, heat exchangers 110, phase separators 115, phenol extraction units 125, dehydration columns 130, and product columns 140, which can be as discussed and described above or elsewhere herein. Rather than locating the phenol extraction unit(s) 125 between the phase separator(s) 115 and the dehydration column 130, however, the phenol extraction unit 125 can be located between the dehydration column 130 and the product column 140. As such, the crude product via line 119 can be introduced to the dehydration column 130 where at least a portion of any water can be removed to produce a dehydrated product via line 233 and the separated water via line 131.

The dehydrated product in line 233 can have a concentration of aromatic amine(s) ranging from a low of about 96 wt %, about 97 wt %, or about 98 wt % to a high of about 99 wt %, about 99.9 wt %, about 99.99 wt %, or about 99.999 wt %. The dehydrated product in line 233 can have a concentration of water ranging from a low of about 1 ppmwt, about 100 ppmwt, or about 200 ppmwt to a high of about 1,000 ppmwt, about 1,500 ppmwt, or about 2,000 ppmwt. The dehydrated product in line 233 can have a phenol concentration ranging from about 1 part per million by weight (ppmwt) to about 2,500 ppmwt. For example, the amount of phenol in the dehydrated product in line 233 can range from a low of about 1 ppmwt, about 50 ppmwt, or about 100 ppmt to a high of about 800 ppmwt, about 1,000 ppmwt, about 1,200 ppmwt, or about 1,600 ppmwt. The dehydrated product in line 233 can have a combined impurity concentration (excluding phenol and water) ranging from about 1 ppmwt to about 15,000 ppmwt. For example, the amount of impurities other than phenol and water in the crude product in line 119 can range from a low of about 1 ppmwt, about 100 ppmwt, or about 250 ppmwt to a high of about 1,000 ppmwt, about 5,000 ppmwt, or about 8,000 ppmwt.

The dehydrated product via line 233 can be introduced to the phenol extraction unit 125 to produce a phenol-lean dehydrated product or phenol-lean product via line 237. The phenol-lean product in line 237 can have a phenol concentration of less than about 200 ppmwt, less than about 100 ppmwt, less than about 50 ppmwt, less than about 30 ppmwt, less than about 20 ppmwt, less than about 10 ppmwt, less than about 5 ppmwt, less than about 3 ppmwt, less than about 2 ppmwt, or less than about 1 ppmwt. The phenol-lean product in line 237 can have an aromatic amine(s) concentration ranging from a low of about 96 wt %, about 97 wt %, or about 98 wt % to a high of about 99 wt %, about 99.9 wt %, about 99.99 wt %, or about 99.999 wt %. The phenol-lean product in line 237 can have a water concentration ranging from a low of about 1 ppmwt, about 100 ppmwt, or about 200 ppmwt to a high of about 1,000 ppmwt, about 1,500 ppmwt, or about 2,000 ppmwt. The phenol-lean product in line 237 can have a combined impurity concentration (excluding phenol and water) ranging from a low of about 3 ppmwt, about 100 ppmwt, or about 250 ppmwt to a high of about 1,000 ppmwt, about 5,000 ppmwt, or about 15,000 ppmwt.

The phenol-lean product via line 237 can be introduced to the product column 140 to produce the aromatic amine product via line 143 and the impurities via line 141. The aromatic amine product in line 143 and the impurities in line 141 can be as discussed and described above or elsewhere herein.

Figure 3:
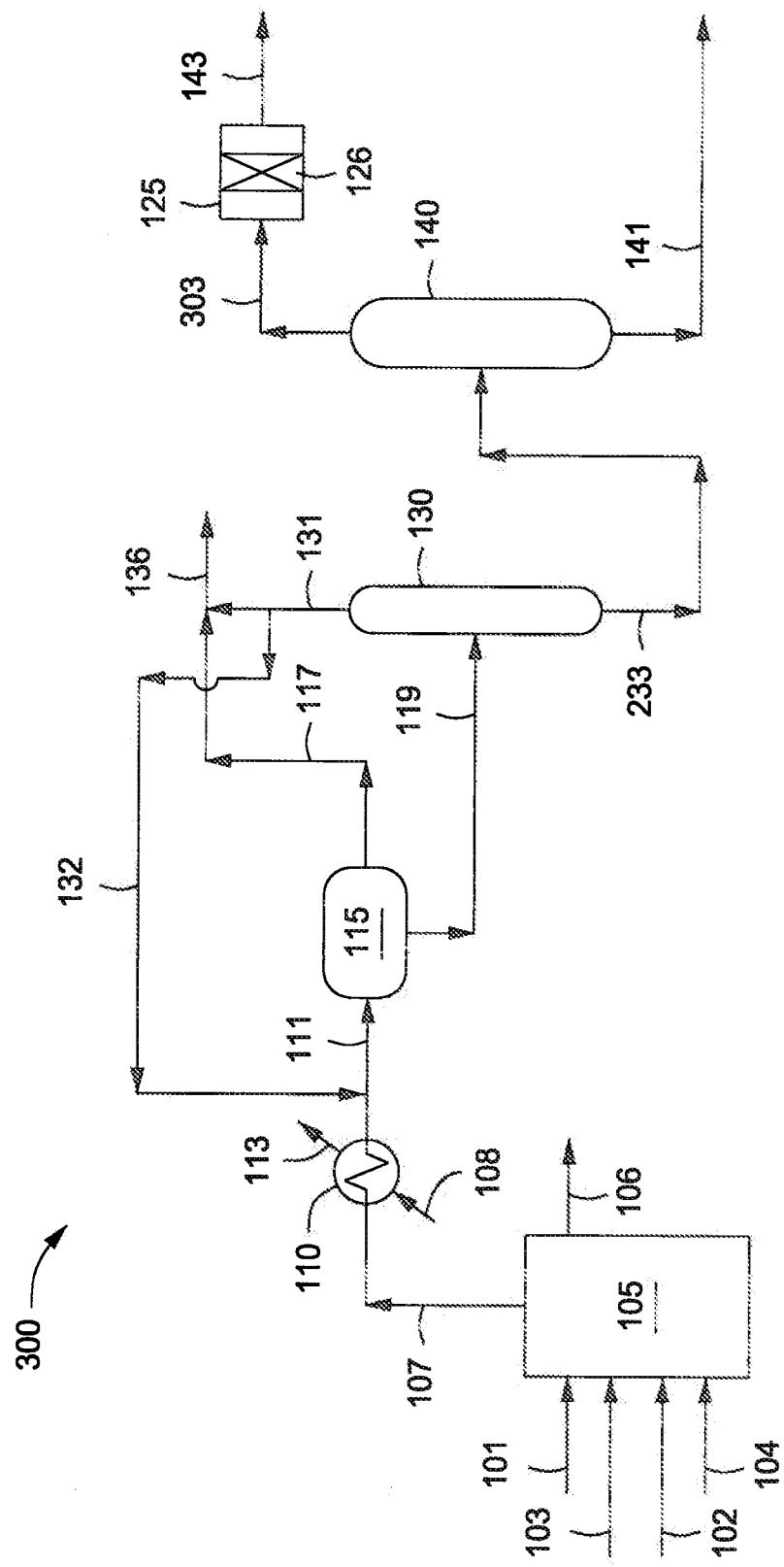
FIG. 3 depicts a schematic of another illustrative system for producing a crude aromatic amine and separating phenol therefrom, according to one or more embodiments described.

FIG. 3 depicts a schematic of another illustrative system 300 for producing a crude aromatic amine and separating phenol therefrom, according to one or more embodiments. The system 300 can include the one or more hydrogenation reactors 105, heat exchangers 110, phase separators 115, phenol extraction units 125, dehydration columns 130, and product columns 140, which can be as discussed and described above with reference to FIG. 1. Rather than locating the phenol extraction unit(s) 125 between the phase separator(s) 115 and the dehydration column 130 (as shown in FIG. 1) or between the dehydration column 130 and the product column 140 (as shown in FIG. 2) the phenol extraction unit 125 can be located downstream of the product column 140. As such, a dehydrated product recovered via line 233 from the dehydration column 130 (as discussed and described above with reference to FIG. 2) can be introduced to the product column 140.

The product column 140 can separate the impurities via line 141 from the dehydrated product as discussed and described above with reference to FIGS. 1 and 2. A crude aromatic amine product containing phenol can be recovered via line 303 from the product column 140. The crude aniline product in line 303 can have an aromatic amine(s) concentration ranging from a low of about 96 wt %, about 97 wt %, or about 98 wt % to a high of about 99 wt %, about 99.9 wt %, about 99.99 wt %, or about 99.999 wt %. The crude aromatic amine product in line 303 can have a phenol concentration ranging from a low of about 1 part per million by weight (ppmwt) to about 3,000 ppmwt. For example, the amount of phenol in the crude aromatic amine product in line 303 can range from a low of about 1 ppmwt, about 50 ppmwt, or about 100 ppmwt to a high of about 800 ppmwt, about 1,000 ppmwt, about 1,200 ppmwt, about 1,600 ppmwt, or about 2,200 ppmw. The crude aromatic amine product in line 303 can have a water concentration ranging from a low of about 1 ppmwt, about 100 ppmwt, or about 200 ppmwt to a high of about 1,000 ppmwt, about 1,500 ppmwt, or about 2,000 ppmwt. The crude aromatic amine product in line 303 can have a concentration of impurities (excluding water and phenol) of less than about 1,000 ppmwt, less than about 500 ppmwt, less than about 250 ppmwt, less than about 100 ppmwt, less than about 50 ppmwt, less than about 25 ppmwt, less than about 15 ppmwt, less than about 10 ppmwt, less than about 5 ppmwt, or less than about 1 ppmwt.

The crude aromatic amine product via line 303 can be introduced to the phenol extraction unit 125 to produce a final or purified aromatic amine product via line 141. The aromatic amine product via line 141 can be as discussed and described above or elsewhere herein.

Figure 4:
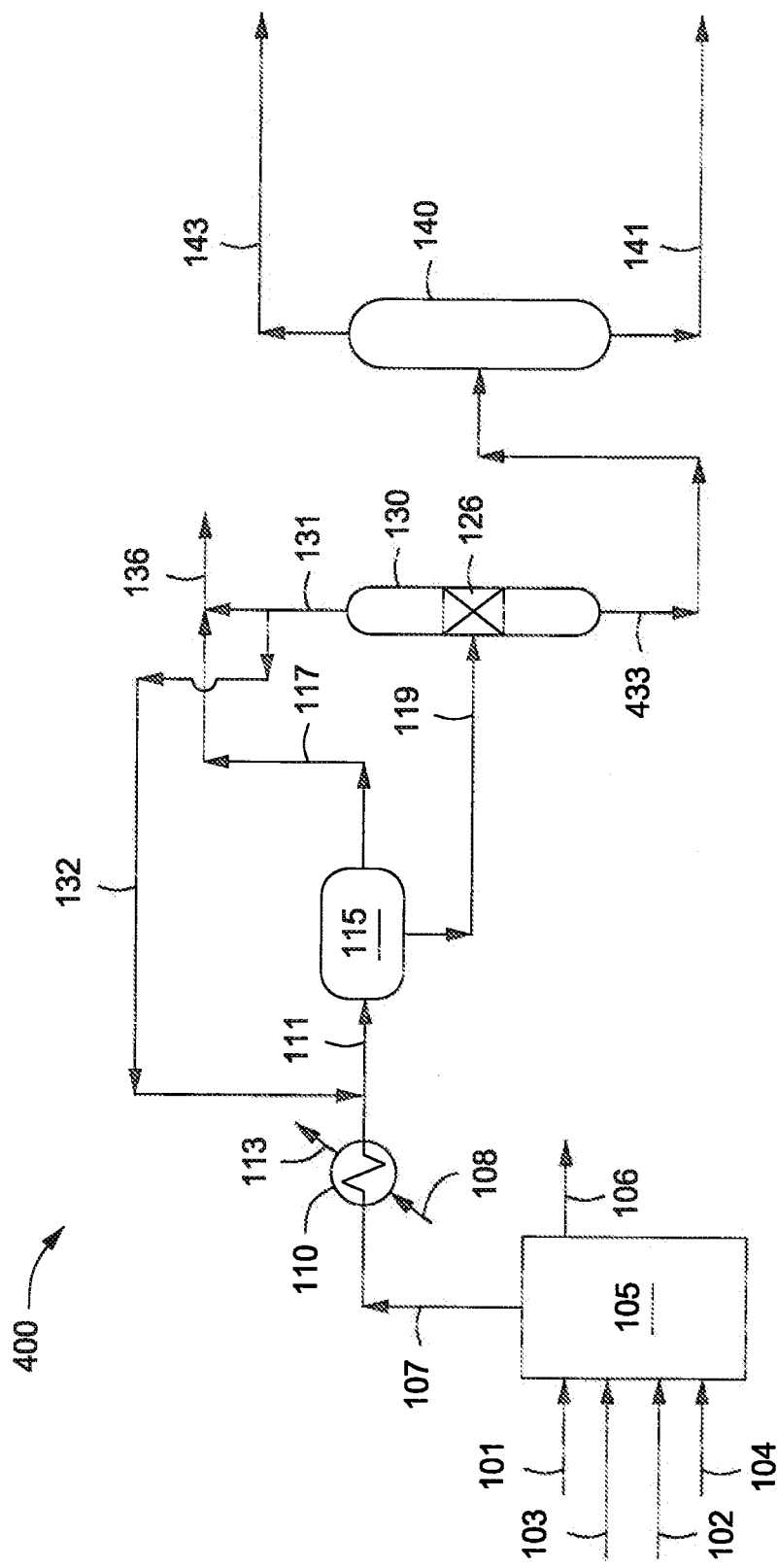
FIG. 4 depicts a schematic of another illustrative system for producing a crude aromatic amine and separating phenol therefrom, according to one or more embodiments described.

FIG. 4 depicts a schematic of another illustrative system 400 for producing a crude aromatic amine and separating phenol therefrom, according to one or more embodiments. The system 400 can include the one or more hydrogenation reactors 105, heat exchangers 110, phase separators 115, phenol extraction units 125, dehydration columns 130, and product columns 140, which can be as discussed and described above with reference to FIG. 1. Rather than locating the phenol extraction unit(s) 125 between the phase separator(s) 115 and the dehydration column 130 (as shown in FIG. 1) or between the dehydration column 130 and the product column 140 (as shown in FIG. 2) or downstream of the product column 140 (as shown in FIG. 3), the one or more ion exchange materials 126 can be located within the dehydration column 130. As such, the crude product via line 119 can be introduced to the dehydration column 130 and contacted with the one or more ion exchange materials 126 within the dehydration column 130 to produce a phenol-lean dehydrated product or phenol-lean product via line 433. The phenol-lean product via line 433 can be introduced to the product column 140 to produce the waste or heavies byproduct via line 141 and the aromatic amine product via line 143.

The phenol-lean product in line 433 can have a phenol concentration of less than about 200 ppmwt, less than about 100 ppmwt, less than about 50 ppmwt, less than about 30 ppmwt, less than about 20 ppmwt, less than about 10 ppmwt, less than about 5 ppmwt, less than about 3 ppmwt, less than about 2 ppmwt, or less than about 1 ppmwt. The phenol-lean product in line 433 can have an aromatic amine(s) concentration ranging from a low of about 96 wt %, about 97 wt %, or about 98 wt % to a high of about 99 wt %, about 99.9 wt %, about 99.99 wt %, or about 99.999 wt %. The phenol-lean product in line 433 can have a water concentration ranging from a low of about 1 ppmwt, about 100 ppmwt, or about 200 ppmwt to a high of about 1,000 ppmwt, about 1,500 ppmwt, or about 2,000 ppmwt. The phenol-lean product in line 433 can have a combined impurity concentration (excluding phenol and water) ranging from a low of about 1 ppmwt, about 100 ppmwt, or about 250 ppmwt to a high of about 1,000 ppmwt, about 5,000 ppmwt, or about 15,000 ppmwt.

Although not shown, in addition to or in lieu of locating or otherwise disposing the one or more ion exchange materials 126 within the dehydration column 130, the one or more ion exchange materials 126 can be located or otherwise disposed within a separate vessel or other container. At least a portion of the crude product introduced via line 119 to the dehydration column 130 can be taken off as a side draw, for example, introduced to the separate vessel or other container, contacted with the one or more ion exchange materials 126 to produce the phenol lean product, and returned or recycled back to the dehydration column 130.

In one or more embodiments, the systems 100, 200, 300 and/or 400 can include at least two phenol extraction units 125 located between different components or units within the system(s) and/or within one or more components or units within the system(s). For example, the system 100 can include a first phenol extraction unit 125 located between the phase separator 115 and the dehydration column 130 and a second phenol extraction unit 125 located between the dehydration column 130 and the product column 140 or downstream of the product column 140. In another example, the system 100 can include a first phenol extraction unit 125 located between the phase separator 115 and the dehydration column 130, a second phenol extraction unit located between the dehydration column 130 and the product column 140, and a third phenol extraction unit located downstream of the product column 140. Any number of phenol extraction units 125 can be used within the systems 100, 200, 300, and/or 400. For example, the system 100, 200, 300, and/or 400 can include 1, 2, 3, 4, or more phenol extraction units 125.

In one or more embodiments, two or more phenol extraction units 125 can be arranged in parallel with respect to one another. In such an arrangement, when the capacity of the ion exchange material nears exhaustion, e.g., the ion exchange material no longer removes a sufficient amount of phenol from the crude product in a first phenol extraction unit 125, the introduction of the phenol containing product to the first phenol extraction unit 125 can be stopped and switched to the second phenol extraction unit 125. The ion exchange material in the exhausted first phenol extraction unit 125 can be replaced and/or regenerated while the second phenol extraction unit 125 operates to remove phenol. When the capacity of the ion exchange material in the second phenol extraction unit 125 nears exhaustion the introduction of the phenol containing product can be stopped and switched back to the first phenol extraction unit 125. The ion exchange material in the second phenol extraction unit 125 can be replaced and/or regenerated while the first phenol extraction unit removes phenol and so on.

Although not shown, in one or more embodiments, the phenol extraction unit 125 can be located within any one of the systems 100, 200, 300, and 400 between the hydrogenation reactor 105 and the one or more heat exchangers 110. In one or more embodiments, the phenol extraction unit 125 can be located between two or more heat exchangers 110. In one or more embodiments, the phenol extraction unit 125 can be located between the one or more heat exchangers 110 and the phase separator 115. In one or more embodiments, a phenol extraction unit 125 can be located upstream of the phase separator in any one or more of the systems 100, 200, and 300. Also not shown, in one or more embodiments, the one or more ion exchange materials 126 can be located within the product column 140 of any one or more of the systems 100, 200, 300, and 400.

Although not shown, in one or more embodiments, any one or more of the systems 100, 200, 300, and 400 can further include one or more other columns. For example, any one or more of the systems 100, 200, 300, and/or 400 can include a rectifier column. The rectifier column can be located, for example, upstream or downstream of the product column 140. If the system 100, 200, 300, and/or 400 includes additional columns such as a rectifier column, the phenol extraction unit can be located before and/or after any additional column(s). In another example, if the system 100, 200, 300, and/or 400 includes additional columns, the one or more ion exchange materials 126 can be located within those one or more additional columns.

Embodiments described herein further relate to any one or more of the following paragraphs:

1. A method for producing one or more aromatic amines, comprising: hydrogenating one or more aromatic nitro compounds to produce a reaction product comprising one or more aromatic amines, water, and phenol; and contacting the reaction product with one or more ion exchange materials to produce an aromatic amine product that contains less phenol than the reaction product, wherein the one or more ion exchange materials are solid, semi-solid, or a combination thereof.

2. The method according to paragraph 1, further comprising separating at least a portion of the water from the reaction product to produce a dehydrated reaction product.

3. The method according to paragraph 2, wherein the water is separated prior to contacting the reaction product with the one or more ion exchange materials, after contacting the reaction product with the one or more ion exchange materials, or both.

4. The method according to any one of paragraphs 1 to 3, wherein the reaction product further comprises one or more impurities other than the water and phenol, and the method further comprises separating at least a portion of at least one of the one or more impurities other than the water and phenol from the reaction product, wherein the at least a portion of at least one of the one or more impurities other than the water and phenol is separated prior to contacting the reaction product with the one or more ion exchange materials, after contacting the reaction product with the one or more ion exchange materials, or both.

5. The method according to paragraph 4, wherein the one or mire impurities comprise nitrobenzene, nitrotoluene, dinitrotoluene, dinitrobenzene (DNB), polynitrobenzenes, methylcyclopentane, methylcyclohexane, mononitrotoluenes, nitroxylenes, cyclohexanone, cyclohexanol, cyclohexylamine, cyclohexylaniline, diphenylamines, phenylene diamines, cyclohexylidene aniline, toluidenes, xylidenes, toluene, benzene, or any combination tereof.

6. The method according to any one of paragraphs 1 to 5, wherein the one or more aromatic nitro compounds in the reaction product comprise nitrobenzene, and wherein the one or more aromatic amines in the reaction product comprise aniline.

7. The method according to any one of paragraphs 1 to 6, wherein the one or more ion exchange materials comprise one or more ion exchange resins.

8. The method according to any one of paragraphs 1 to 7, wherein the one or more ion exchange materials comprise one or more functional groups selected from the group consisting of $OH^-$, $F^-$, $HCO_3^-$, $Cl^-$, $Br^-$, $NO_3^-$, $HSO_4^-$, $PO_4^{3-}$, $CrO_4^{2-}$, $CO_3^-$, and $SO_4^{2-}$.

9. The method according to any one of paragraphs 1 to 8, wherein the one or more ion exchange materials are in the form of pellets, beads, granules, flakes, spheres, cubes, blocks, fibers, filaments, threads, or any combination thereof.

10. The method according to any one of paragraphs 1 to 9, wherein the one or more ion exchange materials comprise a polymer based on a cross-linked styrene divinylbenzene copolymer containing quaternary ammonium groups.

11. The method according to any one of paragraphs 1 to 10, wherein the particles have an average cross-sectional length of about 0.01 mm to about 2 mm.

12. The method according to any one of paragraphs 1 to 11, wherein the one or more ion exchange materials have an average pore diameter of about 100 Å to about 500 Å, a pore volume of about 0.1 ml/g to about 1 $mu_g$, and a surface area of about 10 $m^2/g$ to about 50 $m^2/g$.

13. The method according to any one of paragraphs 1 to 11, wherein the one or more ion exchange materials have an average pore diameter of about 100 Å to about 500 Å.

14. The method according to any one of paragraphs 1 to 11, wherein the one or more ion exchange materials have a pore volume of about 0.1 ml/g to about 1 ml/g.

15. The method according to any one of paragraphs 1 to 11, wherein the one or more ion exchange materials have a surface area of about 10 $m^2/g$ to about 50 $m^2/g$.

16. The method according to any one of paragraphs 1 to 15, wherein the reaction product is at a temperature of about 20° C. to about 100° C. when contacted with the one or more ion exchange materials.

17. The method according to any one of paragraphs 1 to 16, wherein the reaction product is contacted with the one or more ion exchange materials at a rate of about 0.1 $m^3$ reaction product per 1 $m^3$ ion exchange material per hour to about 30 $m^3$ reaction product per 1 $m^3$ ion exchange material per hour.

18. A method for producing one or more aromatic amines, comprising: hydrogenating one or more aromatic nitro compounds to produce a reaction product comprising from about 15 wt % to about 80 wt % of one or more aromatic amines, about 25 wt % to about 85 wt % water, about 1 ppmwt to about 1,500 ppmwt phenol, and about 1 ppmwt to about 15,000 ppmwt of one or more impurities, wherein the one or more aromatic nitro compounds comprise nitrobenzene and the one or more aromatic amines comprise aniline, and wherein the impurities comprise nitrobenzene, nitrotoluene, dinitrotoluene (DNT), dinitrobenzene (DNB), polynitrobenzenes, methylcyclopentane, methylcyclohexane, mononitrotoluenes, nitroxylenes, cyclohexanone, cyclohexanol, cyclohexylamine, cyclohexylaniline, diphenylamines, phenylene diamines, cyclohexylidene aniline, toluidenes, xylidenes, toluene, or any combination thereof; separating at least a portion of the water from the reaction product to produce a dehydrated product comprising about 98 wt % or more of the one or more aromatic amines and less than about 2,000 ppmwt water; separating at least a portion of the impurities from the reaction product to produce an impurity-lean product comprising about 99 wt % or more of the one or more aromatic amines and less than about 1,000 ppmwt of the impurities; contacting, at a temperature ranging from about 20° C. to about 100° C., at least one of the reaction product, the dehydrated product, and the impurity-lean product with one or more ion exchange materials to produce a product that contains less phenol than the reaction product, wherein the one or more ion exchange materials are solid, semi-solid, or a combination thereof.

19. The method of paragraph 18, wherein the one or more ion exchange materials comprise one or more ion exchange resins.

20. The method according to paragraph 18 or 19, wherein the one or more ion exchange materials comprise one or more functional groups selected from the group consisting of $OH^-$, $F^-$, $HCO_3^-$, $Cl^-$, $Br^-$, $NO_3^-$, $HSO_4^-$, $PO_4^{3-}$, $CrO_4^{2-}$, $CO_3^-$, and $SO_4^{2-}$.

21. The method according to any one of paragraphs 18 to 20, wherein the one or more ion exchange materials comprises a polymer based on a cross-linked styrene divinylbenzene copolymer containing quaternary ammonium groups.

22. The method according to any one of paragraphs 18 to 21, wherein the particles have an average cross-sectional length of about 0.01 mm to about 2 mm.

23. The method according to any one of paragraphs 18 to 22, wherein the one or more ion exchange materials have an average pore diameter of about 100 Å to about 500 Å, a pore volume of about 0.1 ml/g to about 1 ml/g, and a surface area of about 10 $m^2/g$ to about 50 $m^2/g$.

24. The method according to any one of paragraphs 18 to 22, wherein the one or more ion exchange materials have an average pore diameter of about 100 Å to about 500 Å.

25. The method according to any one of paragraphs 18 to 22, wherein the one or more ion exchange materials have a pore volume of about 0.1 ml/g to about 1 ml/g.

26. The method according to any one of paragraphs 18 to 22, wherein the one or more ion exchange materials have a surface area of about 10 $m^2/g$ to about 50 $m^2/g$.

27. The method according to any one of paragraphs 18 to 26, wherein the reaction product is at a temperature of about 20° C. to about 100° C. when contacted with the one or more ion exchange materials.

28. The method according to any one of paragraphs 18 to 27, wherein the reaction product is contacted with the one or more ion exchange materials at a rate of about 0.1 $m^3$ reaction product per 1 m³ ion exchange material per hour to about 30 m³ reaction product per 1 m³ ion exchange material per hour.

29. A system for producing an aromatic amine, comprising: one or more hydrogenation reactors for hydrogenating one or more aromatic nitro compounds to produce a reaction product comprising one or more aromatic amines, water, and phenol; and one or more phenol extraction units for contacting the reaction product with one or more ion exchange materials to produce an aromatic amine product that contains less phenol than the reaction product, wherein the one or more ion exchange materials are solid, semi-solid, or a combination thereof.

30. The system according to paragraph 29, further comprising one or more phase separators, one or more dehydration columns, one or more product columns, or any combination thereof.

31. The system according to paragraph 30, wherein the one or more phenol extraction units are located upstream from the one or more phase separators, dehydration columns, and product columns.

32. The system according to paragraph 30, wherein at least one of the one or more phenol extraction units are located between at least two of the one or more phase separators, the one or more dehydration columns, and the one or more product columns.

33. The system according to paragraph 30, wherein at least one of the one or more phenol extraction units are located downstream of at least one of the one or more phase separators, the one or more dehydration columns, and the one or more product columns.

34 The system according to paragraph 30, wherein at least one of the one or more phenol extraction units are located within at least one of the one or more phase separators, the one or more dehydration columns, and the one or more product columns.

35. The system of paragraph 29, further comprising one or more phase separators for separating a first portion of the water from the reaction product to produce a reaction product containing less water, wherein the one or more phase separators are located upstream of the one or more phenol extraction units, downstream of the one or more phenol extraction units, or both.

36. The system according to paragraph 29 or 35, further comprising one or more dehydration columns for separating a second portion of any water from the reaction product to produce a dehydrated product comprising about 98 wt % or more of the one or more aromatic amines and less than about 2,000 ppmwt water, wherein the one or more dehydration columns are located upstream of the one or more phenol extraction units, downstream of the one or more phenol extraction units, or both.

37. The system according to paragraph 29 or 35, further comprising one or more dehydration columns for separating a second portion of any water from the reaction product to produce a dehydrated product comprising about 98 wt % or more of the one or more aromatic amines and less than about 2,000 ppmwt water, wherein at least one of the one or more phenol extraction units are located within at least one of the one or more dehydration columns.

38. The system according to any one of paragraphs 29 to 35, further comprising one or more product columns for separating at least a portion of one or more impurities other than the water and phenol from the reaction product to produce an impurity-lean product, wherein the one or more phenol extraction units are located upstream from the one or more product columns, downstream from the one or more product columns, within the one or more product columns, or any combination thereof.

39. The method or system according to any one of paragraphs 1 to 38, wherein the one or more ion exchange materials are disposed within a fixed bed, a fluid bed, or a combination thereof.

40. The method or system according to any one of paragraphs 1 to 39, wherein the one or more ion exchange materials are disposed within a fixed bed, and wherein the fixed bed is supported on one or more support members, between two or more support members, or a combination thereof.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for producing one or more aromatic amines, comprising:
    hydrogenating one or more aromatic nitro compounds to produce a reaction product comprising one or more aromatic amines, water, and phenol;
    separating at least a portion of the water from the reaction product to produce a crude product comprising about 100 ppmwt to about 2,500 ppmwt phenol and about 85 wt % to about 99 wt % aniline; and
    contacting the crude product with one or more ion exchange materials to produce an aniline product that contains less than 50 ppmwt phenol, wherein the one or more ion exchange materials are solid, semi-solid, or a combination thereof.

2. The method of claim 1, wherein the crude product comprises about 0.1 wt % to about 12 wt % water.

3. The method of claim 2, wherein the crude product comprises about 93 wt % to about 99 wt % aniline and about 0.1 wt % to about 5 wt %-water.

4. The method of claim 1, wherein the reaction product further comprises one or more impurities other than the water and phenol, and the method further comprises separating at least a portion of at least one of the one or more impurities other than the water and phenol from the reaction product, wherein the at least a portion of at least one of the one or more impurities other than the water and phenol is separated prior to contacting the reaction product with the one or more ion exchange materials, after contacting the reaction product with the one or more ion exchange materials, or both.

5. The method of claim 1, wherein the aniline product contains less than 10 ppmwt phenol.

6. The method of claim 1, wherein the aniline product contains less than 1 ppmwt phenol.

7. The method of claim 1, wherein the one or more ion exchange materials comprise one or more functional groups selected from the group consisting of $OH^-$, $F^-$, $HCO_3^-$, $Cl^-$, $Br^-$, $NO_3^-$, $HSO_4^-$, $PO_4^{3-}$, $CrO_4^{2-}$, $CO_3^-$, and $SO_4^{2-}$.

8. The method of claim 1, wherein the one or more ion exchange materials are in the form of pellets, beads, granules, flakes, spheres, cubes, blocks, fibers, filaments, threads, or any combination thereof.

9. The method of claim 1, wherein the one or more ion exchange materials comprise a polymer based on a cross-linked styrene divinylbenzene copolymer containing quaternary ammonium groups.

10. The method of claim 1, wherein the one or more ion exchange materials have an average pore diameter of about 100 Å to about 500 Å, a pore volume of about 0.1 ml/g to about 1 ml/g, and a surface area of about 10 m$^2$/g to about 50 m$^2$/g.

11. The method of claim 1, wherein the reaction product is contacted with the one or more ion exchange materials at a rate of about 0.1 m$^3$ reaction product per 1 m$^3$ ion exchange material per hour to about 30 m$^3$ reaction product per 1 m$^3$ ion exchange material per hour.

12. A method for producing one or more aromatic amines, comprising:
hydrogenating one or more aromatic nitro compounds to produce a reaction product comprising from about 15 wt % to about 80 wt % of one or more aromatic amines, about 25 wt % to about 85 wt % water, phenol, and about 1 ppmwt to about 15,000 ppmwt of one or more impurities, wherein the one or more aromatic nitro compounds comprise nitrobenzene and the one or more aromatic amines comprise aniline, and wherein the impurities comprise nitrobenzene, nitrotoluene, dinitrotoluene (DNT), dinitrobenzene (DNB), polynitrobenzenes, methylcyclopentane, methylcyclohexane, mononitrotoluenes, nitroxylenes, cyclohexanone, cyclohexanol, cyclohexylamine, cyclohexylaniline, diphenylamines, phenylene diamines, cyclohexylidene aniline, toluidenes, xylidenes, toluene, or any combination thereof;
separating at least a portion of the water from the reaction product to produce a dehydrated product comprising about 98 wt % or more of the one or more aromatic amines, about 100 ppmwt to about 2,500 ppmwt phenol, and less than about 2,000 ppmwt water;
separating at least a portion of the impurities from the reaction product to produce an impurity-lean product comprising about 99 wt % or more of the one or more aromatic amines, about 100 ppmwt to about 2,500 ppmwt phenol, and less than about 1,000 ppmwt of the impurities;
contacting, at a temperature ranging from about 20° C. to about 100° C., at least one of the dehydrated product and the impurity-lean product with one or more ion exchange materials to produce a product that contains less than 50 ppmwt phenol, wherein the one or more ion exchange materials are solid, semi-solid, or a combination thereof.

13. The method of claim 12, wherein the aniline product contains less than 1 ppmwt phenol.

14. The method of claim 13, wherein the one or more ion exchange materials comprise one or more functional groups selected from the group consisting of $OH^-$, $F^-$, $HCO_3^-$, $Cl^-$, $Br^-$, $NO_3^-$, $HSO_4^-$, $PO_4^{3-}$, $CrO_4^{2-}$, $CO_3^-$, and $SO_4^{2-}$.

15. The method of claim 12, wherein the one or more ion exchange materials comprises a polymer based on a cross-linked styrene divinylbenzene copolymer containing quaternary ammonium groups.

16. The method of claim 12, wherein the ion exchange material has an average pore diameter of about 100 Å to about 500 Å, a pore volume of about 0.1 ml/g to about 1 ml/g, and a surface area of about 10 m$^2$/g to about 50 m$^2$/g.

* * * * *